United States Patent [19]
Rabito et al.

[11] Patent Number: 5,647,363
[45] Date of Patent: *Jul. 15, 1997

[54] AMBULATORY CLEARANCE FUNCTION MONITOR

[75] Inventors: Carlos A. Rabito, Medford; Richard H. Moore, Concord, both of Mass.

[73] Assignee: The General Hospital Corporation, Boston, Mass.

[*] Notice: The term of this patent shall not extend beyond the expiration date of Pat. No. 5,301,673.

[21] Appl. No.: 225,646

[22] Filed: Apr. 11, 1994

Related U.S. Application Data

[63] Continuation-in-part of Ser. No. 793,781, Nov. 18, 1991, Pat. No. 5,301,673.

[51] Int. Cl.$^6$ ........................................... A61B 6/00
[52] U.S. Cl. ..................... 128/659; 128/633; 128/665
[58] Field of Search ........................... 128/633, 653.1, 128/653.4, 653.3, 654, 659, 662, 664, 665; 356/39–41

[56] References Cited

U.S. PATENT DOCUMENTS

| | | |
|---|---|---|
| 3,827,427 | 8/1974 | Knoll . |
| 4,092,980 | 6/1978 | Frank et al. . |
| 4,243,884 | 1/1981 | Avera, Jr. . |
| 4,329,986 | 5/1982 | Babb . |
| 4,380,240 | 4/1983 | Jobsis et al. . |
| 4,682,604 | 7/1987 | Fymat et al. . |
| 4,798,955 | 1/1989 | Rosenthal . |
| 4,889,991 | 12/1989 | Ramsey et al. . |
| 4,893,013 | 1/1990 | Denen et al. . |
| 4,908,202 | 3/1990 | Schultz . |
| 4,992,255 | 2/1991 | Pardridge ............. 128/654 X |
| 5,054,915 | 10/1991 | Kanda et al. . |
| 5,154,176 | 10/1992 | Kanda . |
| 5,233,997 | 8/1993 | Klein et al. ............. 128/654 X |
| 5,301,673 | 4/1994 | Rabito et al. ............. 128/659 |
| 5,335,660 | 8/1994 | Dumoulin ............. 128/653.4 X |

FOREIGN PATENT DOCUMENTS

| | | |
|---|---|---|
| 82 30 0522 | 2/1982 | European Pat. Off. . |
| 86 30 2549 | 4/1986 | European Pat. Off. . |
| 26 41 039 | 9/1976 | Germany . |
| 3245778 | 6/1984 | Germany . |

OTHER PUBLICATIONS

Bak et al., "Optimal CdTe–Detector Mounting for Evaluation of the Kidney Function with $^{99m}$Tc–DTPA", 1982, Proc. III World Congress of Nuclear Medicine and Biology, Paris, pp. 609–913.

Blaufox et al., "Measurement of Effective Renal Plasma Flow in Man by External Counting Methods", 1967, Jour. Nucl. Med., vol. 8, pp. 77–85.

Bojsen et al., "Portable Cadmium Telluride Detectors and Their Applicability for External Measurement of $^{51}$Cr–EDTA Clearance*", 1981, Intl. J. Applied Radiation and Isotopes, vol. 32, pp. 719–727.

Carrie et al., "Creatinine: An Inadequate Filtration Marker in Glomerular Diseases", 1980, Am. Jour. Med., vol. 69, pp. 177–182.

Casey et al., "GRF Measurement by Simulating Constant Infusion with Data Acquired Using a CdTe Detector a Feasiblity Study", 1986, Nuclear Med. Communications, vol. 7, pp. 811–818.

(List continued on next page.)

*Primary Examiner*—Angela D. Sykes
*Assistant Examiner*—Samuel Gilbert
*Attorney, Agent, or Firm*—Choate, Hall & Stewart

[57] ABSTRACT

Accurate and continuous monitoring of clearance function is obtained by determining the depletion of a labelled substance from the extracellular body fluid using an external monitor which detects from within the defined tissue volume. The detector of the external monitor is contained within a barrier which functions to both exclude external influences and to functionally isolate the volume of extracellular fluid to be monitored.

38 Claims, 5 Drawing Sheets

OTHER PUBLICATIONS

Cerretelli et al., "Cadmium Telluride $^{133}$Xe Clearance Detector for Muslce Blood Flow Stuides", Feb. 1978, IEEE Transactions on Nuclear Science, vol. NS–25, No. 1, pp. 620–623.

Chantler et al., "Estimation of Glomerular Filtration Rate from Plasma Clearance of 51–Chromium Edetic Acid", 1972, Arch. Dis. Child, vol. 47, pp. 613–ff.

Earle et al., "A Simplified Clinical Procedure for Measurement of Glomerular Filtration Rate and Renal Plasma Flow", 1946, Proc. Soc. Exp. Biol. Med., vol. 62, pp. 262–269.

Price, "Comparison of Creatinine Clearance to Inulin Clearance in the Determination of Glomerular Filtration Rate", 1972, Urology, vol. 107, pp. 339–340.

Rossing et al., "The Glomerular Filtration Rate Determined with Tc–DTPA and a Portable Cadmium Telluride Detector", 1978, Scand. Jour. Clin. Lab. Invest., vol. 38, pp. 23–28.

Sapirstein et al., "Volumes of Distribution and Clearances of Intravenously Injected Creatinine in the Dog", 1955, Am. Jour. Physiol., vol. 181, pp. 330–ff.

Shemesh et al., "Limitations of Creatine as a Filtration Marker in Glomerulopathic Patients", 1985, Kidney Int., vol. 18, pp. 830–838.

Walser et al., "Creatinine Measurements Often Yield False Estimates of Progression in Chronic Renal Failure", 1988, Kidney Int., vol. 34, pp. 412–418.

AMBULATORY CLEARANCE FUNCTION MONITOR

The present application is a continuation-in-part of application U.S. Ser. No. 07/793,781, filed 18 Nov. 1991, and issued on 12 Apr. 1994 as U.S. Pat. No. 5,301,673, the contents of which are incorporated herein by reference.

BACKGROUND OF THE INVENTION

This invention relates to monitoring organ function. Some organs, such as, for example the kidney or the liver, remove or clear substances from body fluids. The performance of such a clearance organ can be determined by monitoring the clearance by the organ of a labelled substance from the body fluids, for example.

The kidney is one such clearance organ that removes substances from body fluids. Acute renal failure ("ARF") as a complication of medical, obstetrical and multiple surgical conditions represents an important health problem. Currently patients suffering from ARF have a survival rate of only 50%. The pathogenesis of renal failure remains undefined, and there are no clear approaches for its prevention and treatment. In the early stages of renal failure patients show no symptoms and feel no discomfort. Diagnosis can be made by analyzing the body fluids to determine whether the kidneys are maintaining the expected levels of one or more substances.

Because of the abruptness of the renal impairment in patients having ARF, their clinical status following the onset of renal failure is determined largely by their prior state of health and the nature of the insult that led to the renal failure. Hypoperfusion of the kidney is a frequently recognized insult leading to ARF in the setting of trauma, surgery, hemorrhage or dehydration. Continuous and precise monitoring of the cardiopulmonary function in such settings has long been available and has helped in restoring the normal circulatory status of the acute patient, but estimation of the renal function conventionally is carried out by such relatively crude means as measurement of urine output and determination of plasma creatinine level.

Renal function is conventionally determined by measuring the levels of substances in the urine or the serum, or both. Either technique can be made quantitative, but they have not become widely used for monitoring because, among other reasons, they require taking multiple samples from the patient and the sample analysis is time-consuming and costly.

In one accurate but technically difficult approach to determining clearance rate, a substance is introduced to the patient by continuous intravenous infusion until an equilibrium is reached at which the plasma level of the substance (as determined by analysis of plasma samples) is steady, at which point the infusion rate equals to the rate of loss in the urine (Earle et al., 1946, *Proc. Soc. Exp. Biol. Med.*, Vol. 62, pp. 262 ff.)

In another approach, the glomerular filtration rate is calculated from an analysis of the rate of disappearance of a labelled substance from the plasma after a single intravenous injection. Following an equilibration period, the clearance of the labelled substance is determined by measuring the level of the label remaining in a series of blood samples taken over a period of several hours; the injected substance can be radiolabelled and the amount of the radiolabel detected in the samples (Sapirstein et al., 1955, *Am. Jour. Physiol.*, Vol. 181, pp. 330 ff.; Chantler et al., 1972, *Arch. Dis. Child.*, Vol. 47, pp. 613 ff.) or the quantity of the substance remaining in each of the series of blood samples can be determined by gas chromatography after extraction of the substance from the serum (H.-U. Schulz, 1990, U.S. Pat. No. 4,908,202). The non-endogenously produced substance inulin may be an ideal filtration marker for GFR determination, and it has remained the "gold standard". Inulin is in limited supply and difficult to measure.

External monitors for measuring renal function have been suggested, but have not come into wide use for a variety of reasons. In the suggested approaches, a radiolabelled substance is administered to the patient, and then a radiation detector is positioned so that it is exposed to radiation from the labelled substance in the blood or urine. External monitors have been positioned adjacent the head, and on the chest of the patient to be monitored, to bring the detector near the blood stream; or adjacent the kidney or urinary bladder, to bring the detector near the urine. The apparatus can be expensive, patient movement can be restricted during monitoring, the patient can be uncomfortable, and background noise generally limits the accuracy and reliability of the measurements.

Rossing et al., 1978, *Scand. Jour. Clin. Lab. Invest.*, Vol. 38, pp. 23–28; and Casey et al., 1986, *Nucl. Med. Comm.*, Vol. 7, pp. 811–818, describe using external detectors placed upon the patient's chest to determine the clearance of $^{99m}$Tc-DTPA from the blood as a measure of renal function. In these approaches, one plasma sample is taken in order to convert the external rate constant to plasma clearance. Because the background noise to signal ratio is fairly high, and renal function, as expressed by GFR, can be determined by taking the slope of the data values at intervals longer than about 30 to 60 minutes.

Bak et al., 1982, Proc. III World Congress of Nuclear Medicine and Biology, Paris: 1982, pp. 609–13, describes positioning a CdTe detector at the back of the leg 10 cm below the knee for analyzing $^{99m}$DTPA clearance as a measure of renal function.

In another approach, Junges German Patent No. 3,245,778 describes using a gamma camera with three detectors, one focused on each kidney and the third on the urinary bladder, to measure quantity of a radiolabelled substance removed by the kidneys.

These methods are inadequate for monitoring renal function in the acute patient. Current methods of measuring renal function have poor time resolution, and undetected or late-detected renal failure accounts for substantial mortality. There is at present no reliable method for continuous and near real-time monitoring of renal function.

SUMMARY OF THE INVENTION

We have discovered that clearance of a substance from a subject's body, or from a portion of a subject's body, can be continuously and accurately monitored in real-time by using an external monitor arranged to detect the presence of the substance within a defined tissue volume to determine the depletion of the substance. The term "real time" refers to methods in which the time interval between collection of data and data output is one the order of minutes.

A device for measuring depletion of a detectable substance from a subject, includes a detector having means for responding to a signal generated from a substance within extracellular fluid of the subject. At least one barrier encloses the detector and at least a portion of the subject's body part. The barrier defines a constant volume of extracellular fluid within which the signal is detected and the barrier is adapted to prevent signal external to the constant volume portion from reaching the detector. A signal processing means is connected to the detector and may include a preamplifier, discriminator, and microcomputer and power supply in electrical communication with the signal processing means. The signal processing means is operatively associated with the detector which indicates a quantity of the detectable substance within the defined constant volume of extracellular fluid. The signal processing means determines depletion of the detectable substance in the constant defined volume from a time change in quantity of the detectable substance within the constant volume of extracellular fluid.

The device further has an aperture defined in the barrier for limiting signal from the body to that signal capable of entering the aperture. In one embodiment, a barrier is a cuff that encloses at least a portion of the body part of the subject containing the defined tissue volume. In an alternate embodiment, the barrier encloses at least a portion of a body part that is substantially capable of transmitting light, such as the earlobe or the fingertip.

The detector may comprise a continuous, annular element capable of enclosing at least a portion of the body part of the subject containing the defined tissue volume. Preferably, this annular detector is encased within the cuff.

The detector is capable of detecting a signal from a radioactive label and is preferably a scintillation counter, most preferably a cadmium telluride or sodium iodide detector. The detector may also be capable of detecting a signal from a fluorescent label and may be a photodetector that includes a source of exciting radiation. The detector may also be capable of detecting a substance that ocurrs naturally within the subject, or a substance that does not occur naturally within the subject. For example, the detector may be capable of detecting non-naturally-occurring benzene or naturally-occurring creatinine. In other embodiments, a plurality of spaced-apart detectors are positioned circumferentially around a body extremity such as a limb.

The device is lightweight and compact and is easily worn by the patient, and the patient can be free to move about during clearance function monitoring according to the invention. The invention thus provides for near real-time continuous monitoring of the clearance function in ambulatory patients as well as immobilized patients.

In some preferred embodiments the detectable substance is injected into the subject, for example intravascularly. Following injection at a particular intravascular site, the labelled substance becomes progressively more uniformly distributed in the blood, and begins to pass from the intravascular space to the extravascular space. And, clearance of the labelled substance commences when fluid carrying the substance reaches the clearance organ or clearance organ system. Some time after the initial injection, the concentration of the substance reaches an equilibrium in the fluids within the intravascular and the extravascular spaces. The intravascular and extravascular spaces are together referred to here as the extracellular space, and the fluids within the extracellular space are together referred to here as the extracellular space. For a substance such as $^{99m}$Tc-DTPA, for example, useful for determining glomerular filtration rate, the equilibration of the substance within the extracellular space of the upper arm of an adult requires about 15 to 20 minutes' time. Once equilibrium is reached, the extracellular fluid concentration of the substance and, hence, the intensity of the label, falls at a rate dependent upon the rate of the clearance function.

Preferably, the substance is radiolabelled, and a radiation detector is positioned adjacent to a limb and within a substantially radiopaque barrier encircling a portion of a limb, so that radiation substantially only from label within the enclosed body portion reaches the detector.

In preferred embodiments the labelled substance includes a radiolabelled agent which is cleared substantially only by the organ whose clearance function is to be monitored, such as for example $^{99m}$Tc-DTPA, $^{51}$Cr-EDTA, $^{125}$I-iothalamate and $^{125}$I-hippurate for determining kidney function; the radiopaque barrier is made of lead or a lead containing composition and is configured at least in part to form a cylindrical enclosure about a body portion such as a portion of a limb, for example the upper arm, and the soft tissues of the body portion are compressed slightly to ensure an approximately constant extracellular fluid volume in the enclosed space during the monitoring period.

In some preferred embodiments the detector is provided with signal processing and display means for computing and indicating a measure of the clearance function, and more preferably with means for recomputing the measure and updating the display at intervals. The signal processing means can report the measure of clearance function in near real-time, that is, it can update the clearance function measure in short time intervals, for example in the order of several minutes; or the signal processing means can store sampling information continuously or at sampling intervals for later retrieval and analysis. The signal processing means can include means for selecting a sampling interval, for example, a counting interval for radiation detection; preferably the duration of the sampling interval can be preset or can be varied over the course of the monitoring period, and more preferably it can be increased as necessary to provide for a calculation of the clearance rate within a desired statistical confidence limit.

In some embodiments the apparatus includes a plurality of detectors; the detectors can be adapted to detect different detectable substances, or to provide replicate samples of detection of a single detectable substance.

The invention can be used to monitor clearance function in a variety of settings including, surgery, drug titration, organ transplants, early diabetes detection, cardiac failure, and septic shock.

DETAILED DESCRIPTION OF THE INVENTION

A clearance function monitor according to the invention includes a detector, positionable on the body surface or positionable noninvasively in a body cavity, that is capable of detecting the presence of a detectable substance in adjacent and proximate tissues, and includes means for defining a tissue volume within which the detectable substance can be so detected. The substance can be specific for clearance by any of a variety of organs that perform a clearance function, or that metabolize a detectable substance, for example, the liver, the kidney, the thyroid, the brain or bone.

The detector is sensitive to energy radiating from the detectable substance, and the means for defining the tissue volume can include a barrier, substantially opaque to the radiation, that has defined in it an opening limiting the direction from which the energy can pass to the sensible part of the detector. For example, the detector can be a radioactivity detector and the detectable substance radioactive. The barrier generally surrounds the detector. The geometry and dimensions of the opening in relation to the sensible portion of the detector generally determines the shape and dimensions of the space from which detectable radiation can reach the detector.

It will be appreciated that not all radiation reaching the detector by way of the opening will have followed an undeflected course from the detectable substance. Generally, less deflected radiation can be expected to have a higher energy at the detector than more deflected radiation. It will also be appreciated that the capacity of the radiation to pass through the tissues depends, among other factors, upon the initial energy and type of the particular radiation, and upon the opacity of the tissues to the particular radiation. Thus, a further limit on the dimensions of the defined tissue volume from which detectable radiation can reach the detector can be provided, for example, by using a discriminator to reject radiation reaching the detector below (or above) a selected threshold energy level. The effect of these approaches is to substantially exclude scattered radiation from detection.

As an alternative or in addition to an opening as described above, the means for defining the tissue volume may include a second barrier that is substantially opaque to the radiation, for at least partly enclosing a portion of the subject's body containing the defined tissue volume to be sampled. For a radioactive substance and a radiodetector, this body-part enclosing barrier can be a radiopaque sheet, such as a flexible lead composition, that can be affixed in a generally cylindrical configuration about a portion of a limb of the subject. The detector can be situated within this enclosing barrier and an opening in the enclosing barrier can be provided for passage of the radiation to the sensible part of the detector.

Figure 1:
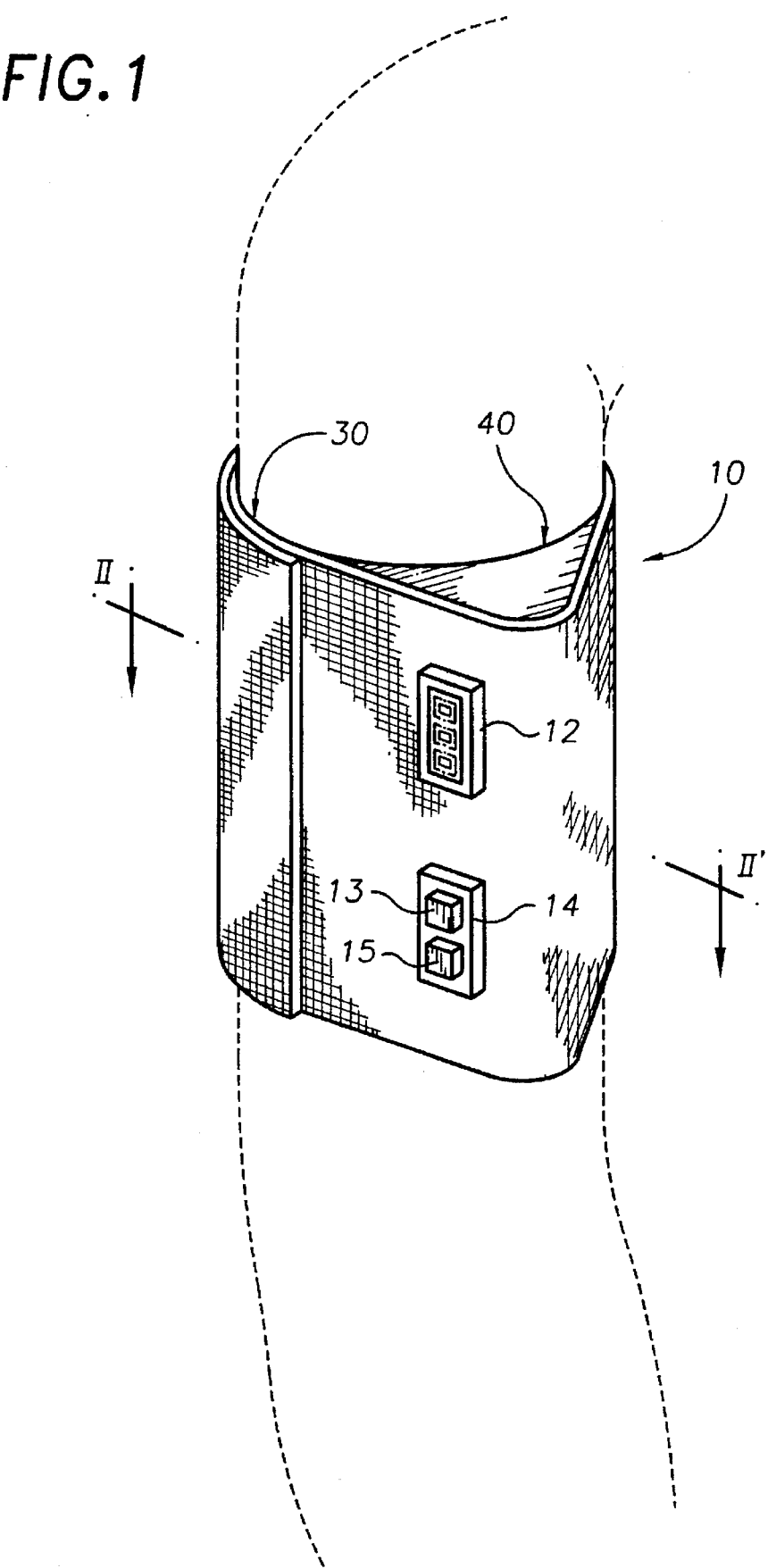
FIG. 1 is a perspective view of a clearance function monitor of the invention, showing the apparatus in place on an upper arm of a patient.
Figure 2:
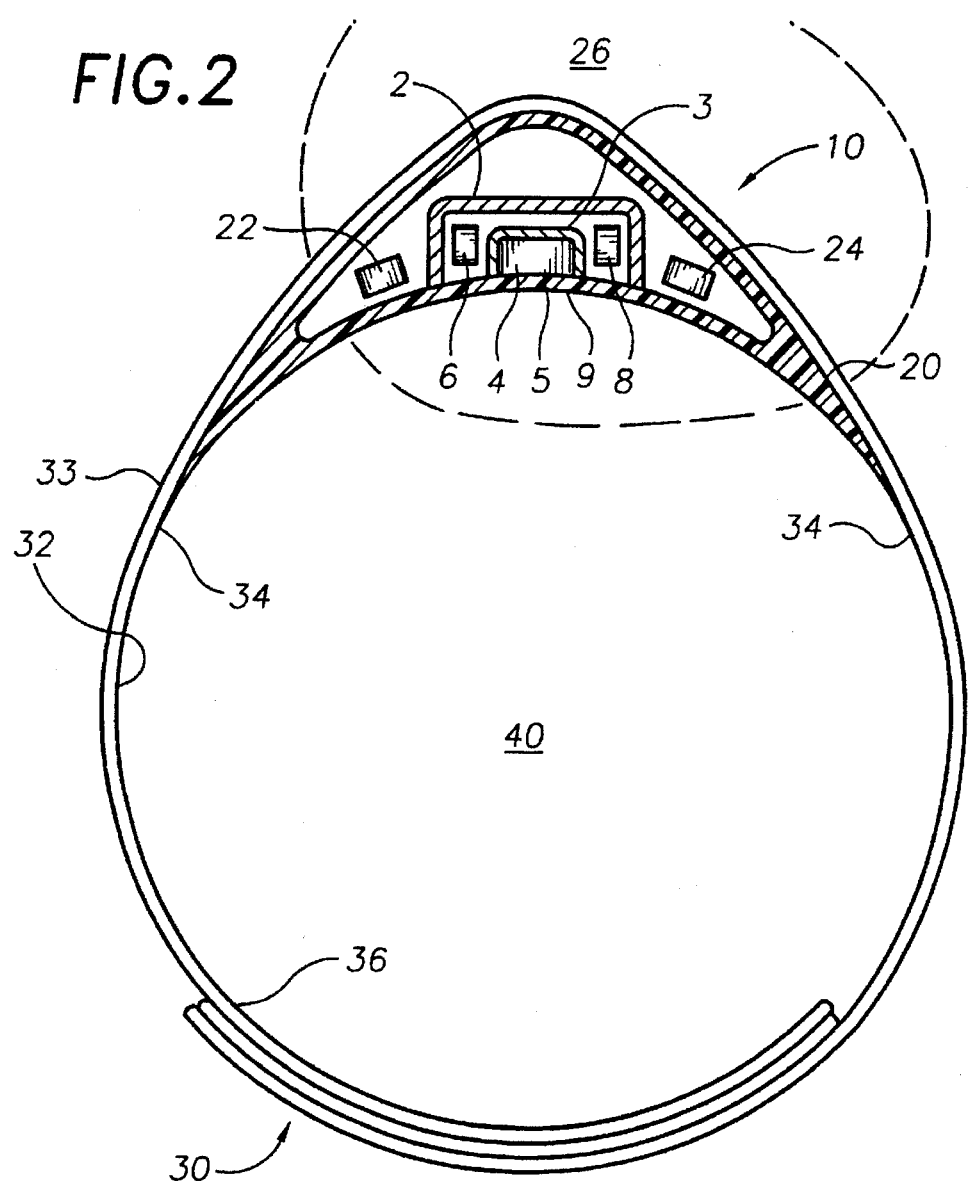
FIG. 2 is a sectional view thru the apparatus of FIG. 1, showing positions of the various components.
Figure 3:
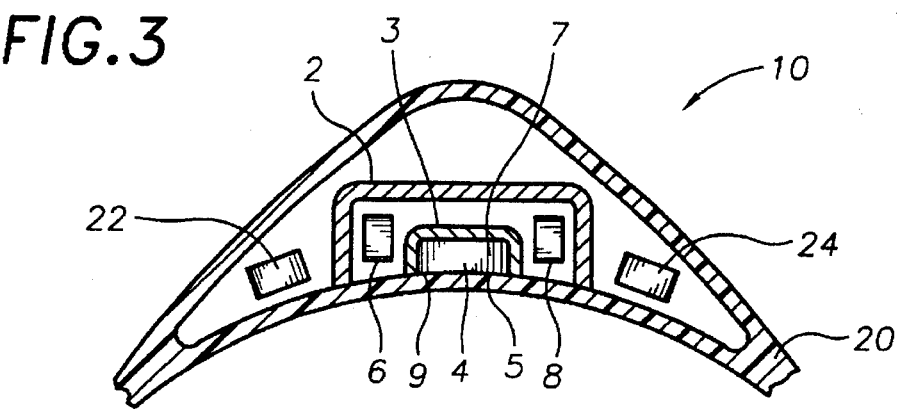
FIG. 3 is a sectional view thru the apparatus of FIG. 1, showing the position of the electrical components in an enlargement of the portion within the broken circle in FIG. 2.

An external monitor according to one embodiment of the invention having a first barrier with an aperture in addition to a body-part enclosing second barrier, is shown in place on a patient's upper arm in perspective view in FIG. 1, in sectional view in FIG. 2, and in a more detailed sectional view in FIG. 3.

The apparatus generally includes detector instrumentation carried in an instrumentation housing, shown generally at 10, and a flexible barrier or cuff 30 wrapped about and enclosing a cylindrical portion 40 of the patient's upper arm. A digital display 12, and a control console 14, including an on/off switch 13 and a microcomputer reset switch 15, are mounted in a readily accessible place on an outer surface of the instrumentation housing 10.

With reference now also to FIG. 2, the detector and associated electrical power supply and instrumentation are mounted in a support 20 of molded plastic in the shape generally of a hemicylinder. A sheet aluminum box 2, secured within the support 20, contains radiation detector 4 and some associated signal processing devices, including preamplifier 6 and discriminator 8, that are operatively associated with the detector. Box 2 has dimensions about 1 cm×2 cm×5 cm, and provides a continouus electrical shield around the detector and its associated electronics. Box 2 is lined with a detector shielding layer 3 of lead about 2 mm thick. Detector 4 is mounted in box 2 with its sensible part 5 facing inward (that is, generally toward the center of the arm portion 40). The detector may be of any shape, i.e., square, rectangular, trapezoidal, and the like. In the embodiment illustrated, detector 4 is about 0.16 cm in diameter. In other embodiments (See, for example FIG. 7) the detector may be larger.

Detector 4 is shielded by a barrier 3, consisting of a wall 7 layer of lead thick enough to be substantially opaque to detectable radiation. One wall layer of detector shield 3 is missing, or is partially missing, generally forming an opening 9 adjacent the sensible part 5 of the detector. This opening preferably is co-extensive with the area of the sensible part 5 of the detector. The other walls 7 of the barrier 3 are closed. This configuration of the detector shield 3 ensures that the detector 4 is sensible substantially only to radiation reaching the detector through plastic support 20 by way of the opening 9.

Also encased within support 20 are a microcomputer 22 and a power source 24; these parts, and the electrical connections among them and with the controls 14 and display 12 are padded with and immobilized within the support 20 by elastomer foam 26.

A body part-enclosing second barrier 30 is formed by at least one sheet 32 of vinyl lead disposed on a surface of the hemicylindrical support 20 closest to the skin of the subject. Optionally, a second sheet 33 is disposed on a surface of the support furthest away from the skin. Sheets 32, 33 extend beyond the edges 34 of the arch of the hemicylinder to form the skirt 36 of the second barrier 30.

The second barrier 30, as shown for example in FIG. 2, forms a generally cylindrical shape that is open at the ends. The second barrier, in this embodiment, is shaped like a conventional blood pressure cuff and encloses a generally cylindrical tissue volume. The detector 4 preferably is located midway the length of the cuff, that is, at approximately equal distances from the open ends. The shield 3 has the effect of limiting the sources of radiation that can reach the detector 4 by way of the opening 9 in the walls 7 of detector shield 3.

Specifically, shield 3 ensures that the detector is sensitive substantially only to radiation from radiolabel in body fluids within the enclosed tissue volume defined by second barrier 30. Although some quantity of radiation may enter the enclosed space from sources located beyond the ends of the cylinder, that is, from farther up or farther down the patient's arm, in the form of scattered radiation, that quantity is comparatively very small, and the scattered radiation represents a decreased energy at the detector, resulting in a decreased signal strength, which can be rejected by a discriminator. A preferred length for the second barrier in relation to the diameter of the enclosed tissue volume depends upon the geometry and dimensions of the opening, as discussed generally above. For example, the second barrier should be long enough so that substantially no unscattered radiation can pass through the opening in the detector shield from detectable substances (or from other sources) beyond the open ends of the second barrier.

Figure 6:
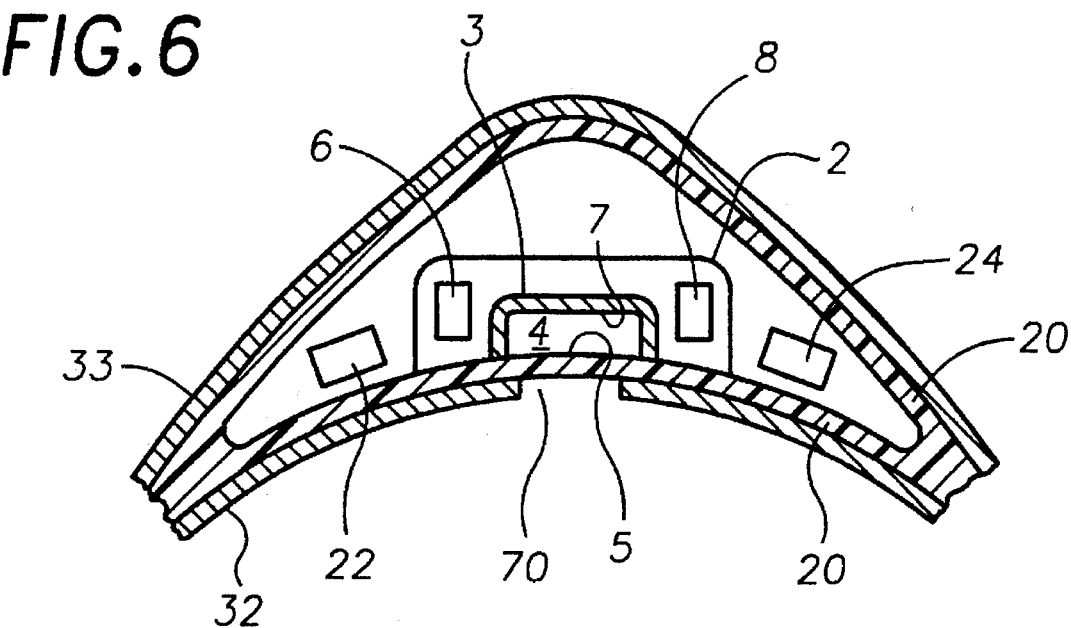
FIG. 6 is a sectional view thru a second embodiment of the apparatus of FIG. 2, showing the position of the vinyl lead opening in an enlargement of the same portion that is within the broken circle in FIG. 2.

Referring now to FIG. 6, in which all reference numbers are identical to those previously except where indicated, vinyl lead sheet 32 has defined in it an opening 70, whose area may be co-extensive with the area of sensible portion 5 of detector 4. Sensible portion 5 is in contact with the bodily extremity by sitting over opening 70. In other embodiments (not shown) opening 70 is smaller in area than the area taken up by sensible portion 5. A thin layer of radiotransparent plastic and/or fabric (not shown) may be affixed to vinyl lead layer 32 to provide a layer adjacent the subject's skin that is more comfortable than a layer of vinyl lead.

Figure 7:
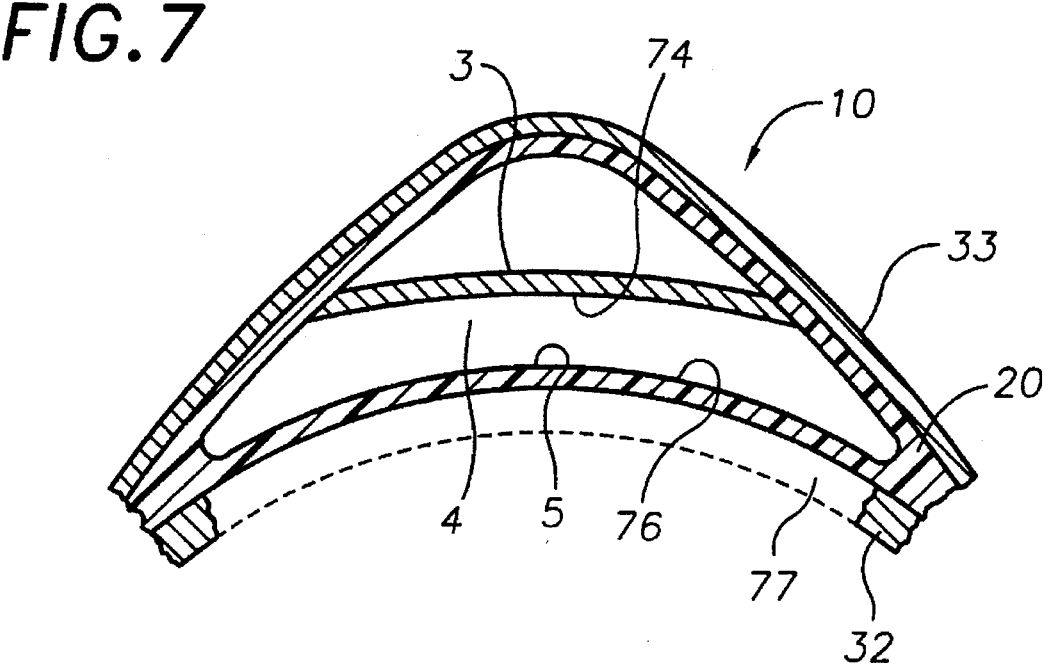
FIG. 7 is a sectional view thru a second embodiment of the apparatus of FIG. 1, showing an enlargement of the same portion that is within the broken circle in FIG. 2.

FIG. 7 illustrates a partial, cut-away cross section of another embodiment in which detector 4 is elongated and whose peripheral surfaces 74,76 define a substantially continuous, annular element. The detector has a sensible part 5 in facing relationship to support 20, in a manner analagous to that shown in FIG. 3. The annular detector's sensible part is in facing relationship to an annular slot 77 defined in the vinyl lead 32 so that the sensible part of the detector is positioned in a manner analogous to that shown in FIG. 6. The detector illustrated in FIG. 7 is designed to mate with a second barrier 30, preferably similar to a blood-pressure cuff, so that the detector encircles a patient's extremity (i.e., arm, leg and the like).

Figure 4:
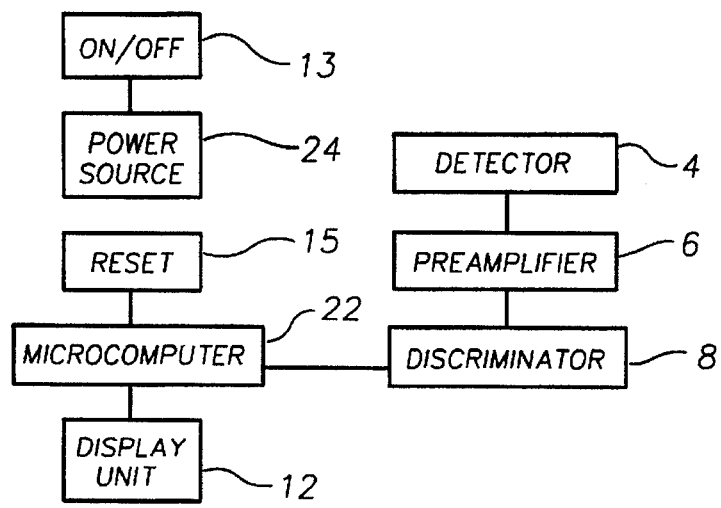
FIG. 4 is a block diagram of the electrical circuitry of a clearance function monitor according to the invention.

Referring now to FIG. 4, the data output signal from the radiation detector 4 passes through preamplifier 6 and discriminator unit 8 to microcomputer 22. Microcomputer 22 is powered by battery power source 24, which is provided with on/off switch 13, and with reset switch 15 for resetting the recording registers for information processing, as described in more detail below. The microcomputer is connected to digital display unit 12 for continuous display of the results of the data analysis, such as a clearance rate.

Figure 5:
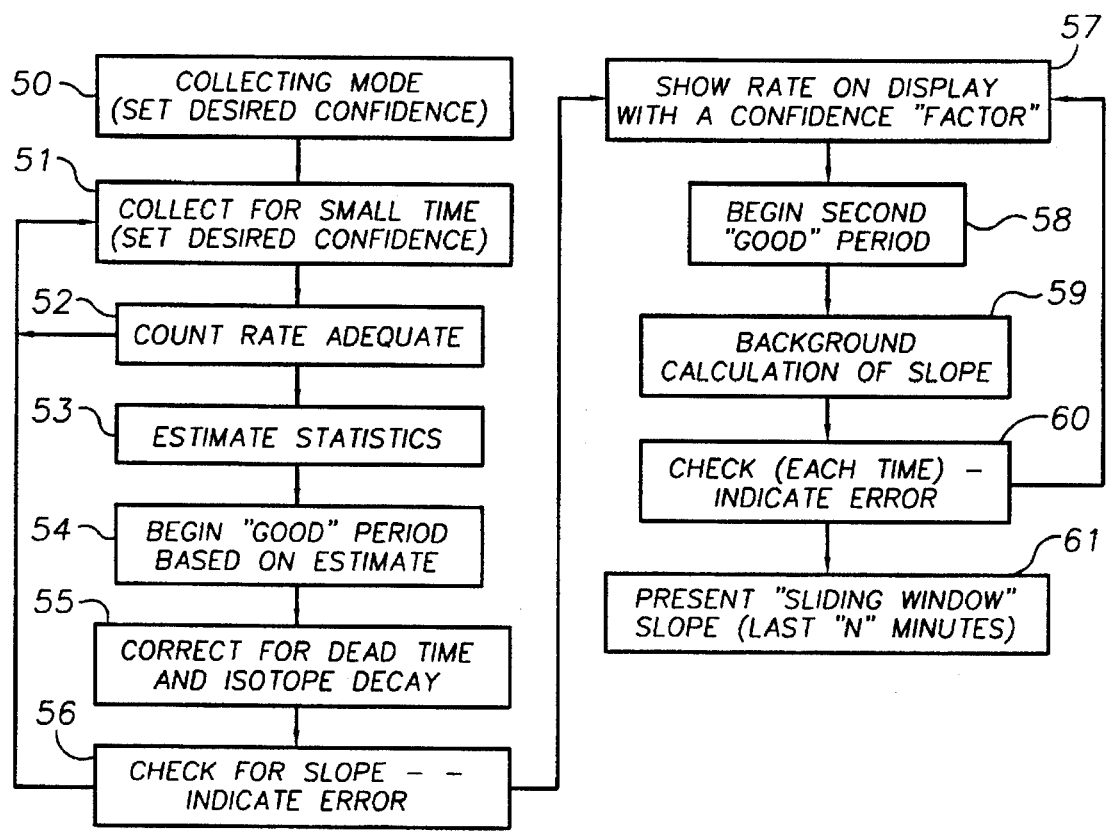
FIG. 5 is a flow diagram showing the microprocessor logic of a clearance function monitor according to the invention.

FIG. 5 shows a flow diagram of the microprocessor logic. The microcomputer uses a single compartment model, as described more fully below, to calculate the clearance function. The collection time 51 can be set for a desired collection interval, but, more preferably, the collecting mode 50 is set to a desired confidence level, and the collection time 51 is adjusted as so that the data are adequate to meet the desired confidence interval. The microcomputer monitors the count rate for data adequacy 52 by estimating the statistics 53, and then adjusts the collection time as necessary. The microcomputer then initiates a collection period 54 based upon the statistical estimate and corrects for dead time and isotope decay 55. Following the conclusion of data collection periods subsequent to the first, the microcomputer calculates and assesses the reliability of the slope, calculates the error 56 and displays the clearance rate with a confidence factor 57. The microcomputer then initiates a next subsequent data collection period 58, performs a calculation of the slope 59 and reassesses the reliability of the slope, calculates the error 60 and displays the new clearance rate with a confidence factor 57. The microcomputer continuously runs the logic cycle as long as it is on, reporting the clearance rate in the manner of a sliding time window, for so long as the level of label remaining in the extracellular fluid is high enough to provide for a statistically acceptable calculation.

A preferred label for use according to the invention is a radiolabel, and the corresponding detector is a radiation detector. For monitoring renal function, for example, a labelled substance is selected that is specifically cleared by the kidneys such as, for example, $^{99m}$Tc-DTPA, $^{51}$Cr-EDTA, and $^{125}$I-sodium iothalamate; and the corresponding detector is a scintillation counting device such as, for example, a cadmium telluride or sodium iodide detector. Other detectors, such as gas, liquid, or solid state detectors, such as cadmium-zinc-telluride, silicon detectors, and germanium detectors, are included within the scope of the invention.

Multiple detectors are also contemplated. At least two detectors and their circuitry may be oriented so that the overall flux of label (i.e., radioactivity, fluorescent light) to the detector: (i) is increased from an isotopic source by intercepting a greater proportion of signal than a single detector; (ii) is stabilized when the detector/source changes position, or when the device moves (i.e., contracts, rotates, expands), or when the label is redistributed within the defined tissue volume. These principles are described with reference to FIG. 8, a cross-section of an embodiment using four spaced-apart radiodetectors 80,82,84,86, placed circumferentially around a body extremity 87 such as a limb.

Each detector has zone of sensitivity 80A, 82A, 84A, 86A defined by the solid lines emanating from each detector, that is determined by its respective opening in the detector shield 3 and in the radio-opaque vinyl lead 32. Each of the detectors detects radioactivity very efficiently from sources closest to it, but as the source moves away from the detector, the signal becomes more attenuated and the efficiency of detection decreases, sometimes to about 10%. For example, a radiactive source close to detector 82 would be counted with close to maximal efficiency (100%) but if the source is moved to near detector 86, the activity detected by detector 82 drops to about 10%.

Figure 8:
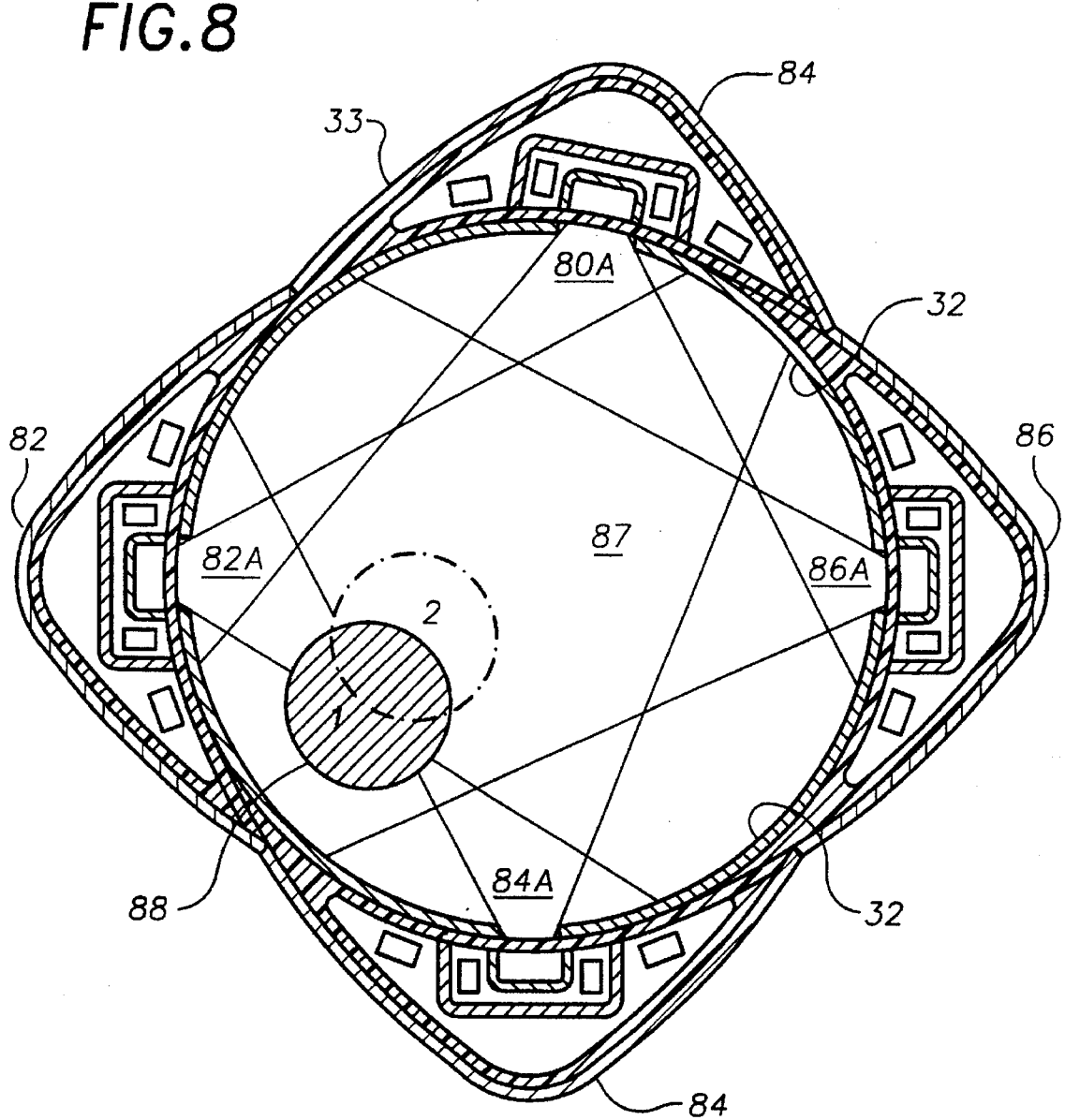
FIG. 8 is a sectional view thru the apparatus of FIG. 1, showing multiple detectors arrayed around a body part.

With reference now to FIG. 8, assume a radioactivity source is located in position 1. If the patient rotates the barrier 30, the position of detector 82 may moves in a counterclockwise direction. Detector 82 is now closer to source 1 and the signal efficiency increases. Detector 84 is now effectively moved away from source 1 and its signal efficieny decreases. The signals from the two detectors compensate one another. Ideally, the detector should be a continuous, annular element surrounding the limb of the subject, as shown in FIG. 7 so that the orientation of the barrier is irrelevant to the signal detection. In an analagous manner, assume a radio-opaque material 88, for example a bone is shown in position 1. In this position, the bone masks signal from both detectors 82 and 84. If the bone moves to position 2 relative to the detectors, detector 82 will be more masked and detector 84 less masked relative to detector 84,86. The signal from detector 82 will decrease and that from detector 84 will increase relative to detectors 84,86. Nonetheless, the overall signal will remain unaffected by the shift in position of the bone relative to the other detectors and their signal will be unchanged. The overall flux measurement is stabilized.

The detectable substance need not be one that is administered to the subject. It could, for example, be a naturally-occurring detectable substance whose quantity is indicative of a condition of the subject or, it could be a non-naturally-occurring detectable substance, such as for example a toxin. The substance need not be a radioactive substance, detectable by a radiodetector. It can be a fluorescent substance, for example, detectable by a photodetector. Such a detection means can include a source of exciting radiation, and the defined tissue volume can include a body part that passes a detectable quantity of the exciting and of the fluorescing light, such as for example an earlobe or a fingertip. An example of a naturally-occurring detectable substance is creatine, useful for determining renal function, which can be detectable by its intrinsic fluorescence. And, benzene, for example, is a toxin that can be detectable by its intrinsic fluorescence. The substance need not be an organic compound; for some clearance functions, for example, detection of gold, iodine or thallium can be useful.

As described above, the tissue volume to be sampled by the detector may be defined by any one or some combination of a variety of means: (i) using a barrier that provides an aperture for passage of radiation from the detectable substance to the sensible part of the detector; and/or (ii) enclosing a portion of a body part within a barrier); and/or (iii) employing a discriminator to reject any signal having an energy that is higher than some upper limit or lower than some lower limit. Further, tissue volume may be limited by exploiting an anatomical characteristic of the body that, in and of itself, limits the tissue volume within which detectable signal may be detected. As an example, a detector positioned within the ear canal and proximate the vascular bed in the ear canal can be an at least partially self limiting sampling tissue space, particularly for fluorescence-based detection.

Where a barrier in the form of a cuff is employed to assist in defining the tissue volume by enclosing a body part, attachment of the cuff to a limb or extremity is preferred over attachment to the body trunk for a variety of reasons. For example, the lower vascular content of a limb relative to the trunk provides a more linear slope after equilibration. A limb is not subject to large variations in blood volume as is a trunk organ such as the heart. Further, the various fluid-filled compartments in a limb are less subject to shifting position as the patient moves about. Other considerations may be pertinent, as well. For instance, the arm, and particularly the upper arm, is preferred for renal function monitoring over the upper leg, because the upper leg is too close to the kidneys and the urinary bladder, making shielding from scattered or direct radiation from cleared labelled substance in those organs difficult. The lower leg is less preferred, although it is farther from the kidneys and bladder, because it has a low flesh to bone ratio and because the lower leg can be particularly susceptible to edema, which would change the fluid volume within the defined tissue space and interfere with accurate determination of clearance.

The device according the invention can be used for continuously monitoring the clearance of a substance from the body or from a portion of the body, and particularly from the extracellular body fluid, and thus for continuously monitoring the performance of a clearance organ or organ system, in a wide variety of settings.

For monitoring of clearance function, a monitoring session can be initiated by injecting the patient intravascularly with a labelled substance that normally is cleared by the particular organ whose performance is to be monitored. The monitoring device according to the invention is affixed to the patient, for example by enclosing a part of the patient's upper arm within the cuff. Once the power is switched on, the detector and signal processor begin to collect and analyze the data reaching the detector from within the enclosed tissue space. After a period of time following the injection, typically 15–20 minutes or less, the labelled substance will have equilibrated in the extracellular space, and thereafter the depletion of the labelled substance (as recorded by progressive decline in the signal reaching the detector) provides a measure of the clearance rate. Depending upon how the microprocessor is set up, the clearance rate can be recalculated every few minutes, providing for near real-time monitoring of the clearance function.

As the labelled substance is cleared, the signal eventually falls to a level too low to provide a statistically acceptable calculation of clearance rate. At this point, a new monitoring session can be initiated by reinjecting the patient with a dose of the labelled substance, and allowing time for equilibration of the added substance in the extracellular space. If more extended monitoring is indicated, successive monitoring sessions can be initiated in this fashion a number of times, to provide for near-continuous monitoring of the organ function over a period of several days.

A substance, or a plurality of substances, can be detectable by different radiation energies. For example, two or more filtration markers can be radiolabelled using labels having two different emission energies. Two or more parameters of a single organ, or the function of two or more organs, can be simultaneously monitored. For example, one labelled substance can be one that is effective for determining GFR, and the other can be one that is effective in determining kidney perfusion rate. Simultaneously monitoring these two markers, using different labels so they can be distinguished, provides information about the kidney function at the nephron level. Or, a labelled substance that is not expected to be cleared can be monitored simultaneously with a labelled substance that is expected to be cleared, and the results compared. The slope of the curve for the non-clearing substance may provide a baseline check on non-clearance related effects that alter the concentration of the detectable substance in the defined tissue volume. For example, a rapid fall in a filtration marker might indicate an increase in GFR, but a simultaneous rapid fall in the signal from a non-clearing agent might indicate an increase in overall tissue fluid, owing for example to edema, rather than to a change in GFR. The plurality of labels could be detected using multiple detectors within an external monitor or by using multiple monitors. In other embodiments, a single detector may be used to sense multiple energy levels, and a discriminator employed to resolve the signals.

EXAMPLE 1

RENAL FUNCTION MONITOR:

A more detailed description of an example of a renal function monitor follows, in which clearance of a radiolabelled injected substance was measured according to the detected radiation according to the invention. The performance of the apparatus was tested by comparison with results obtained using standard techniques.

Detector; Data Collection.

Data collection was performed using a battery-operated, pocket-size lightweight data logger having 32K total RAM (Tattletale, Model V, Onset Computer Corp., N. Falmouth, Mass.). The detector was a 16 mm diameter×2 mm thick cadmium-telluride (Cd-Te) detector (Radiation Monitoring Devices, Watertown, Mass.) connected to a preamplifier and a lower level discriminator. The detector, preamplifier and discriminator units were housed in a 1 cm×2 cm×5 cm aluminum box. The detector was enclosed in a radio-opaque lead shield 3 mm thick, forming a cylindrical container having a 16 mm diameter radio-transparent circular opening in front of the detector. A cuff was constructed over molded plastic having the shape of a hemicylinder. The aluminum box with the detector unit was secured in the center of this plastic skeleton with the sensible part of the detector facing the inner surface of the radio-transparent plastic hemicylinder. The outer surface of the plastic hemicylinder was covered with a 3 mm thick generally rectangular radio-opaque lead-vinyl sheet. The length of the sheet exceeded by several inches the arch of the hemicylinder, forming skirts that can be wrapped about the arm of the patient, so that when positioned on the upper arm of the patient it defines a structure similar to a blood pressure cuff. Once wrapped about the arm of the patient, the cuff forms a shielded cylinder holding the detector adjacent the patient's skin and containing the detector unit within.

Software.

A basic software for the operation of the data logger provides for individually setting the counting time, and the interval between counting periods. In this configuration, the counting intervals were fixed at 59 seconds, permitting 1 second for data processing by the microprocessor within a one-minute repeat interval. The analysis software is based on a single compartment model, as discussed in more detail below.

Treatment Protocol.

All the subjects had a serum creatinine determination done the day before the study. The usual diet was not altered. Weight and height were measured soon after arrival at the treatment facility. Prior to initiation of the renal function tests, an intravenous cannula was inserted in each arm. One cannula was used for injection of radioisotopes, and the other was used for collection of blood samples. Just before a renal scintigraphic study was carried out, the ambulatory renal monitor was wrapped and secured around the arm of the patient, with the detector positioned on the outside of the arm opposite the site of injection, at the level of the deltoid insertion. The instrument was affixed to the skin using double-coated plastic adhesive tape (3M, St. Paul, Minn.). The subject then remained supine in a quiet room until the end of the studies.

Renal Scintigraphy.

A standard renal scan was performed on each patient upon arrival at the treatment facility, using a camera having a large field of view (Gemini 700, General Electric Co., Milwaukee, Wis.) using the general purpose collimator and a computer. After intravenous bolus injection of $^{99m}$Tc-DTPA (0.15 mCi/Kg body wight) multiple digital and analog sequential images were obtained over a time of 32 minutes. In patients having their own kidneys, the images were acquired from the posterior projection with the camera centered at the level of the kidneys. In patients having renal transplant, the images were acquired from the anterior projection with the camera centered at the level of the pelvis. Following injection, a semiquantitative evaluation of the renal blood flow was performed by acquiring 3 second analog images over a time of 2 minutes. This was followed by static analog images (500,000 counts) at 2, 5, 10, 15 and 20 minutes to evaluate the clearance of the tracer from the renal cortex and collecting system. A computer acquisition of the radioangiographic phase of the study was at a rate of 2 seconds per frame for 32 frames. Static quantitation of GFR was obtained by measuring the relative uptake of each kidney on the 2 minute static image after background subtraction.

Glomerular Filtration Rate.

The glomerular filtration rate was calculated from the clearance of $^{125}$I-iothalamate (GLOFIL-125, Iso-Tex Diagnostic Inc., Friendswood, Tex.) measured with a constant-infusion technique and timed collection of urine. Thirty minutes before the study, the subjects received orally 5 mg KI in water. After a priming bolus injection (5 to 20 uCi), a continuous infusion of $^{125}$I-iothalamate (0.3 uCi/ml saline) was given with a minipump (Harvard, Mini—infuser 400, Bard MedSystem Division, North Reading, Mass.) at a rate of 0.05 uCi/min for a total of 6 hours to achieve equilibrium levels close to 1,500 cpm/ml of plasma. The subjects were not permitted to eat during this period but they were encouraged to drink enough water to maintain a urine output of at least 1 ml/min. The priming dose of $^{125}$I-iothalamate was determined by considering a space distribution equal to 20% of the body weight (extracellular fluid). The dose for the subsequent infusion was calculated from the clearance of creatinine, estimated from the serum creatinine levels and considering the age, weight and sex of the subject. With this approach, the rate of excretion of $^{125}$I-iothalamate by the kidneys and the rate of infusion reach euqilibirum after 90 minutes of continuous infusion. Following this equilibration period, a heparinized blood sample (5 ml plus 10 U heparin) was obtained every 30 minutes for a total of 2 to 4 additional hours. Also during this period, several urine samples were obtained by active voiding.

The activity of $^{125}$I-iothalamate in the infused solution, and in the plasma and urine samples was determined in a well gamma scintillation counter as described above. The plasma samples were counted immediately for $^{99m}$Tc-DTPA and after 3 days (to allow for a complete decay of $^{99m}$Tc) for $^{125}$I-iothalamate. Practically all the measurements of glomerular filtration rate were performed from the rate of intravenous infusion and plasma levels (plasma method). After the equilibration period, the plasma levels of $^{125}$I-iothalamate were within 5% of the mean in all but two patients. The glomerular filtration rate in these two patients was determined from the rate of urinary excretion (urine method) and plasma activity. This method, however, shows the largest variability of the two methods, probably owing to large variability in the urine collection. All calculations were standardized for body surface area.

Counting Characteristics of the Apparatus.

To determine the intrinsic counting characteristics of the apparatus, a source of $^{99m}$TcO$_4$-containing between 30 and 40 uCi of activity was counted over 24 hours. The counting efficiency was set at 0.2% with the source of activity placed in front to the detector. When counts were uncorrected for physical decay of the source, the counting rate decreased at the physical half-life expected for $^{99m}$Tc. The time-activity curve was very smooth, indicating little variability in the counting rate. Calculation of the rate constant for this decay at various intervals indicated that the minimal monitoring time required for obtaining a reasonably accurate rate constant depends upon counting time. For example, when the instrument was set to count for a counting time of 9 seconds every ten seconds, the minimal recording time to obtain an accurate rate constant was about 2 minutes; when it was set to a counting time of 59 seconds every 60 seconds, the time to obtain an accurate rate constant was about 20 minutes.

Positioning of the Detector.

One of the basic assumptions in the use of the monitor according to the invention for measurement of GFR is that the volume and characteristic of the space probed by the detector remains relatively constant during the study. For instance, abrupt changes in the volume of this space could be reflected in rapid changes in the counting rate independent of the clearance of the agent. Because the contribution of the intravascular space to the extracellular space changes with the body location and in certain regions (precordial) with the cardiac cycle, the characteristic of the counting rate was determined with the detector placed upon various parts of the body. Large and rapid changes in the counting rate appeared with the detector placed in the precordial region. With the detector placed over the liver, less extreme changes appeared; but the urinary bladder, itself containing a substantial and varying level of label, is nearby, especially when the patient is sitting, and thus contributes to the detected activity. The arm provided the most consistent recording of activity over time; a substantial isolation from extraneous signal can be achieved when the cuff is placed about the upper arm. Moreover, contrary to what is normally expected from the multiple blood sample collection technique, the decrease in activity over time as determined according to the invention, in which the detector is sensitive to label within a defined volume of tissue space containing a defined volume of extracellular fluid, represents the clearance of the agent from a single compartment.

Monitoring of the Renal Function.

To determine the value of the invention for monitoring of renal function, two patients at risk of ARF with serum creatinine $\geq 2$ mg/dl were monitored before, during and after an angiographic procedure. In one patient, no change in the clearance of the tracer was observed during the study, as indicated by a similar rate constant, and no changes were observed either in the urine output and serum creatinine of this patient, even 48 hours after the study. The second patient showed a significant drop in the rate of clearance, commencing during the angiographic procedure and continuing for at least 12 hours thereafter. The rate constant, as measured according to the invention, decreased in this patient from $2.85 \times 10^{-3}$ min$^{-1}$ to $0.2 \times 10^{-3}$ min$^{-1}$; and the serum creatinine in this patient increased from 2.4 to 2.8 mg/dl over the succeeding 12 hours.

The rate of clearance of $^{99m}$Tc-DTPA was also monitored in a patient in an intensive care unit. Although the initial renal function was moderately decreased as shown by a rate constant of $3.5 \times 10^{-3}$ min$^{-1}$ (Normal: $6.5 \times 10^{-3}$ min$^{-1}$), it was also relatively constant. After 5 hours there was a sudden drop in the mean arterial pressure from 97 mmHg to 57 mmHg that required appropriate therapy. Despite a rapid normalization of the blood pressure, there was a decrease in the urine output, first noticed 2 hours later. However, the monitor according to the invention detected the change in the renal function at about the time of or immediately following the hypotensive event, and prefigured the renal failure as measured by the drop urinary output.

The invention was also used to monitor the recovery of renal function in an anuric patient. The activity was relatively constant and the rate constant and urine output were close to zero at the beginning of the study. Two hours later, however, the rate constant began to increase, reaching a value 12 hours later of $1.8 \times 10^{-3}$ min$^{-1}$. This increase in rate constant was followed, with some delay, by an increase in urine output that reached a maximal value 15 hours later of about 300 ml/h.

Thus, the clearance function monitor according to the invention was capable of detecting near real-time changes in renal function, providing an indication of renal function changes earlier than other available tests. Moreover, the method according to the invention directly measures the rate constant for clearance of a glomerular filtration agent from the extracellular space, providing a direct measurement of GFR and eliminating uncertainties usually associated with determining renal function from serum creatinine and urine output.

Direct Determination of Rate Constant:

Conventionally, estimation of GFR after a single injection of a glomerular filtration agent such as $^{51}$Cr-EDTA or $^{99m}$Tc-DTPA is made by obtaining multiple blood samples over a period of several hours. The analysis of the data considers a two compartment model, to include the clearance of the tracer from both the vascular space and the interstitial space. A single compartment model has also been used as an alternative, where the estimation of GFR is made from blood samples obtained after equilibration of the tracer in the vascular and interstitial spaces. The system equations for these models consider linear compartmental systems with constant coefficients (or rate constants $\lambda$).

For clearance from a one compartment system, in which the intravascular and interstitial spaces are considered to be a single compartment, namely the extracellular space, the system equation is:

$$\frac{dq_1}{dt} = -\lambda_{01} + I(t)$$

Where:

q=Compartment size $\lambda_{01}$=Transport rate constant from compartment 1 to the outside (compartment 0)

t=time

I=Input function.

For an instantaneous Input (single injection):

$$I(t)=0$$

and the solution is:

$$q = q_0 e^{-\lambda_{01} t}$$

Resolving the equation in terms of q=volume (ml) and t=1 minute, then $q_1$=GFR. Thus, it is clear that the value of GFR after a single injection of a glomerular filtration agent depends on the compartment size ($q_0$) and the rate constant $\lambda_{01}$. To avoid variability in GFR due to different compartment sizes, the GFR value is ordinarily corrected according to body surface area, or in other terms, $q_0$ is reduced to a standard q value. Then under this condition GFR depends only on the rate constant $\lambda_{01}$ Thus, the estimation of the rate constant for the clearance of an "ideal" glomerular filtration agent from the extracellular space represents a direct measurement of GFR. This concept constitutes a basic principle for the use of the method according to the invention to measure and monitor the renal function.

Under ideal experimental conditions, in which a source of $^{99m}$Tc is located in the center of the cuff, and the system placed over a bench, the minimal time for obtaining accurate measurements of the rate constant can be 2 minutes or less. In the patient, however, the variability of the data owing to "biological" noise as well as to the "instrument" noise and the system equation depend largely on the location of the detector on the patient's body. For instance, when the detector is placed on the precordial area, there is a large variability in the data owing probably not only to changes in the volume, but also to the changes in the position of the cardiac chambers with reference to the detector as the patient moves about. Moreover, because in the precordial location most of the activity recorded originates in the vascular space, the equation that best describes the system corresponds to a two and not to a single compartment system. The monitor according to the invention, can reduce the "biological" noise sufficiently to allows for measurements of the rate constant at intervals of 5 minutes or less, approaching near real-time conditions, and preliminary studies performed using the invention in patients at risk of AFR showed that the instrument can accurately detect near immediate changes in renal function several hours before other parameters becomes abnormal.

One relative limitation in the use of the instrument to monitor renal function is that sudden changes in the volume of the extracellular space, such as, for example, hemorrhage, rapid infusion or loss of large volume of fluid, and the like, may affect the measurement of the rate constant. In such circumstances the measurements can be restarted once a new steady-state is achieved after the cardiovascular status of the patient has been stabilized.

Simultaneous use of the invention and a scintillation camera can provide not only an absolute measurement of the total renal function but also the contribution from each kidney to the total GRF.

Equivalents

The invention has been described with reference to various specific and preferred embodiments and techniques. However, it should be understood that many variations and modifications may be made while remaining within the spirit and scope of the invention.

We claim:

1. A device for measuring depletion of a detectable substance from a subject, comprising:

a detector having means for responding to a signal generated from a substance equilibrated within a subject's extracellular fluid;

at least one barrier enclosing the detector and at least a portion of a body part of the subject, the barrier defining a constant volume of extracellular fluid within which the signal is detected, said at least one barrier adapted to prevent a signal external to the constant volume portion from reaching the detector; and signal processing means for determining a clearance rate of the detectable substance, the signal processing means capable of measuring depletion of a quantity of said detectable substance within the defined constant volume of extracellular fluid.

2. The device of claim 1, wherein the signal processing means determines depletion of said detectable substance in said constant defined volume from a time change in quantity of said detectable substance within said constant volume of extracellular fluid.

3. The device of claim 2, wherein the signal processing means includes means to: (i) obtain a first measure at a first time of the detectable substance in the defined constant volume of extracellular fluid; (ii) obtain a second measure at a second time; (ii) determine a slope of the first and second measures over a time interval; and (iv) determine and express a clearance rate of said detectable substance using the slope of the first and second measures.

4. The device of claim 3, wherein said signal processing means determines and expresses a clearance rate within several minutes of said first measurement.

5. The device of claims 1 or 3, wherein said at least one barrier comprises a cuff that encloses at least a portion of the body part of the subject containing the defined tissue volume.

6. The device of claim 1, wherein said at least one barrier has defined therein an aperture for limiting signal from the subject to that signal capable of entering the aperture.

7. The device of claim 1, wherein said signal processing means includes a preamplifier.

8. The device of claim 7, wherein said signal processing means includes a discriminator.

9. The device of claim 1, wherein the signal processing means comprises a microcomputer and power supply in electrical communication with the signal processing means.

10. The device of claim 1, wherein the detector detects a signal from a radioactive label.

11. The device of claim 10, wherein the detector is a scintillation counter.

12. The device of claim 11, wherein the scintillation counter is a cadmium telluride or sodium iodide detector.

13. The device of claim 1, wherein the detector detects a signal from a fluorescent label.

14. The device of claim 13, wherein the fluorescent detector is a photodetector that includes a source of exciting radiation.

15. The device of claim 14, wherein the barrier encloses at least the portion of the body part that is substantially capable of transmitting light.

16. The device of claim 15, wherein the body part is an earlobe or fingertip.

17. The device of claim 1, wherein the detector detects a substance that occurs naturally within the subject.

18. The device of claim 17, wherein the detector detects creatine.

19. The device of claim 1, wherein the detector detects a substance that does not occur naturally within the subject.

20. The device of claim 19, wherein the detector detects benzene.

21. The device of claim 1, wherein said detector comprises a continuous, annular element enclosing at least the portion of the body part of the subject containing the defined tissue volume.

22. The device of claim 1, wherein the detector includes a plurality of detectors spaced apart from each other around at least the portion of the subject's body part.

23. A portable device for measuring depletion of a detectable substance from a subject comprising:

a subject including a delectable substance;

a barrier having an elongated sheet capable of defining a volume of extracellular fluid when wrapped around an arm, the sheet having a width sufficient to encompass only a part of the arm and length sufficient to wrap around the arm, said barrier having a portion adapted to house a detector and a device for signal processing;

a detector dispersed within said portion for responding to a signal generated from a substance within the defined volume of extracellular fluid; and a signal processing means dispersed within said portion for determining a clearance rate of the detectable substance by measuring depletion over time of a quantity of said detectable substance within the defined volume of extracellular fluid.

24. The device of claim 23, wherein the detectable substance emits radiation.

25. The device of claim 24, wherein said barrier comprises a material substantially opaque to detectable radiation.

26. The device of claim 25, wherein said barrier comprises lead.

27. The device of claim 23, wherein said barrier, detector and signal processing means are portable.

28. The device of claim 23, wherein said barrier has defined therein an opening adjacent to, and co-extensive with, a portion of the detector that is sensitive to the signal.

29. The device of claim 23, wherein said barrier comprises a sheet of vinyl lead and a sheet of radiotransparent material, the radiotransparent material providing a comfortable layer between the arm and the vinyl lead sheet.

30. The device of claim 29, wherein the radiotransparent material comprises plastic.

31. The device of claim 29, wherein the radiotransparent material comprises fabric.

32. A device for measuring renal clearance of a detectable substance from a subject, comprising:

a detector having means for responding to a signal generated from a substance equilibrated within a subject's extracellular fluid;

at least one barrier enclosing the detector and at least a portion of a body part of subject body part, the barrier defining a constant volume of extracellular fluid within which the signal is detected, said at least one barrier adapted to prevent a signal external to the constant volume portion from reaching the detector; and signal processing means for determining a renal clearance rate of the detectable substance, the signal processing means adapted to: (i) obtain a first measurement of a quantity of said detectable substance at a first time, (ii) obtain a second measurement of a quantity of said detectable substance at a second time, (iii) determine a slope of the first and second measurements over a time interval and (iv) determine and express a clearance rate of said detectable substance using the slope of the first and second measurements within several minutes of said first measurement.

33. A device for measuring depletion of a detectable substance from a subject, comprising:

a detector responsive to a signal generated from a detectable substance equilibrated within a subject's extracellular fluid;

at least one barrier enclosing the detector and at least a portion of a body part of the subject, the barrier defining a volume of extracellular fluid within which the signal is detected, said at least one barrier adapted to prevent a signal external to the volume portion from reaching the detector; and signal processing means for determining a clearance rate of the detectable substance by measuring depletion of a quantity of said detectable substance within the defined volume of extracellular fluid further comprising a second detector responsive to a signal generated from a second detectable substance within the defined volume of extracellular fluid, wherein the signal froth the second detectable substance indicates a change in the defined volume of extracellular fluid.

34. A device for measuring depletion of a detectable substance from a subject, comprising:

a detector responsive to a signal generated from a detectable substance equilibrated within a subject's extracellular fluid;

at least one barrier enclosing the detector and at least a portion of a body part of the subject, the barrier defining a volume of extracellular fluid within which the signal is detected, said at least one barrier adapted to prevent a signal external to the volume portion from reaching the detector; and signal processing means for determining a clearance rate of the detectable substance by measuring depletion of a quantity of said detectable substance within the defined volume of extracellular fluid wherein said detector is responsive to multiple signals and further comprising a discriminator for resolving multiple signals, such that the signals generated by the detectable substance may be distinguished from a signal generated by another substance, wherein said signal by said another detectable substance indicates a change in the defined volume of extracellular fluid.

35. The device of claim 33 or 34, wherein said detectable substance is a filtration marker used to monitor glomerular filtration rate and said another detectable substance is a non-clearing agent used to monitor a change in the defined volume of extracellular fluid.

36. A method for measuring depletion of a detectable substance from a subject comprising:

providing a detectable substance to a subject, said detectable substance capable of equilibrating in a subject's extracellular fluid;

allowing said detectable substance to equilibrate in the subject's extracellular fluid;

wrapping a barrier around an upper arm portion of the subject, said upper arm portion defining a constant volume of the equilibrated extracellular fluid, positioning a detector housed within the barrier on the upper arm portion of the subject;

allowing the detector to respond to a signal generated from the equilibrated substance within the defined constant volume;

measuring a response of said detector to the equilibrated substance, the response indicative of the quantity of said detectable substance within the defined constant volume of said equilibrated extracellular fluid; and determining the depletion of said detectable substance from the measurement of a change in the quantity of said substance within the defined constant volume of said equilibrated extracellular fluid without withdrawing a fluid sample from the subject.

37. The method of claim 36, wherein the step of allowing said detectable substance to equilibrate comprises allowing equilibration for 15 to 20 minutes.

38. The method of claim 36, wherein the time interval between the step of measuring a response of said detector to said equilibrated substance and the step of determining the depletion of said substance is in the order of minutes.

* * * * *

UNITED STATES PATENT AND TRADEMARK OFFICE
CERTIFICATE OF CORRECTION

PATENT NO. : 5,647,363
DATED : July 15, 1997
INVENTOR(S) : Rabito, et. al.

It is certified that error appears in the above-identified patent and that said Letters Patent is hereby corrected as shown below:

Column 2, line 59 please delete "one" and insert therefor --on--

Column 4, line 48 please delete "thru" and insert therefor --through--

Column 4, line 50 please delete "thru" and insert therefor --through--

Column 4, line 59 please delete "thru" and insert therefor --through--

Column 4, line 63 please delete "thru" and insert therefor --through--

Column 4, line 66 please delete "thru" and insert therefor --through--

Column 8, line 27 please delete "radiactive" and insert therefor --radioactive--

Column 8, line 33 please delete "moves" and insert therefor --move--

Column 8, line 44 please delete "signal" and insert therefor --signals--

Column 15, line 41 please delete "(ii)" and insert therefor --(iii)--

UNITED STATES PATENT AND TRADEMARK OFFICE
CERTIFICATE OF CORRECTION

PATENT NO. : 5,647,363
DATED : July 15, 1997
INVENTOR(S) : Rabito, et. al.

It is certified that error appears in the above-identified patent and that said Letters Patent is hereby corrected as shown below:

Column 16, line 28 please delete "delectable" and insert therefor --detectable--

Signed and Sealed this

Ninth Day of March, 1999

Attest:

Q. TODD DICKINSON

*Attesting Officer*          *Acting Commissioner of Patents and Trademarks*